United States Patent [19]

Giglia et al.

[11] Patent Number: 4,565,727

[45] Date of Patent: Jan. 21, 1986

[54] NON-WOVEN ACTIVATED CARBON FABRIC

[75] Inventors: Robert D. Giglia, Rye, N.Y.; Edward A. Battistelli, Stratford, Conn.

[73] Assignee: American Cyanamid Co., Stamford, Conn.

[21] Appl. No.: 725,527

[22] Filed: Apr. 23, 1985

Related U.S. Application Data

[63] Continuation-in-part of Ser. No. 531,366, Sep. 12, 1983, abandoned.

[51] Int. Cl.$^4$ ............... B32B 5/16; B32B 7/14; B32B 31/00
[52] U.S. Cl. ................... 428/172; 428/281; 428/283; 428/286; 428/299; 428/297; 428/408; 428/367; 162/146; 210/505; 210/508; 210/509; 210/510; 210/510.1; 55/527; 55/528
[58] Field of Search ............... 428/171, 172, 281, 283, 428/286, 367, 408, 288, 297, 298, 299; 162/146; 210/505, 508, 509, 510; 55/527, 528

[56] References Cited

U.S. PATENT DOCUMENTS

| | | | |
|---|---|---|---|
| 3,500,618 | 3/1970 | Sokol | 55/527 |
| 3,769,144 | 10/1973 | Economy et al. | 428/408 X |
| 3,850,785 | 11/1974 | McQuade et al. | 55/527 X |
| 4,169,911 | 10/1979 | Yoshida et al. | 428/297 |
| 4,217,386 | 8/1980 | Arons et al. | 428/408 X |
| 4,344,775 | 8/1982 | Klein | 428/283 X |
| 4,391,873 | 7/1983 | Brassell et al. | 428/297 |
| 4,397,907 | 8/1983 | Rosser et al. | 428/283 X |
| 4,433,024 | 2/1984 | Eian | 428/408 X |
| 4,472,541 | 9/1984 | Sorenson et al. | 428/408 X |

*Primary Examiner*—George F. Lesmes
*Assistant Examiner*—Nancy A. B. Swisher
*Attorney, Agent, or Firm*—William H. Calnan

[57] ABSTRACT

An air and water vapor permeable, toxic vapor absorptive non-woven fabric material comprising a web-laid sheet containing fibrillated acrylic fiber, and an activated carbon constituent selected from the group consisting of activated carbon fiber, activated carbon particles, and mixtures of activated carbon fiber and activated carbon particles.

4 Claims, No Drawings

NON-WOVEN ACTIVATED CARBON FABRIC

This application is a continuation-in-part, of application Ser. No. 531,366, filed Sept. 12, 1983, now abandoned.

BACKGROUND OF THE INVENTION

The need for protective clothing has long been recognized by both military and commercial personnel. The manufacture and use of certain dangerous chemicals such as pesticides, toxic materials etc. in the form of sprays or mists, gases etc. requires that personnel involved therewith be provided the safest protective clothing available. Protective clothing has, in the past, been manufactured from completely impermeable materials such as plastics or oilskin. These products did not prove sufficient however, due to preventing the egress of heated air and perspiration from the wearer. Other attempts to provide protective clothing involved the use of absorbent charcoal or other materials in particulate form, however, these products also involved difficulties due to the loss of the particulate material over a period of time. The use of quilted woven carbon cloth and adhesives to bind the carbon particles, also was less than commerically successful, see U.S. Pat. Nos. 3,586,596; 3,769,144.

Accordingly, if a fabric configuration could be developed which overcame the disadvantages of previous fabrics, a step forward in the art would be achieved.

SUMMARY OF THE INVENTION

According to the present invention, a non-woven fabric material containing, as the toxic vapor absorptive ingredient therein, activated carbon particles and/or activated carbon fiber, is produced via the wet-laying process, utilizing fibrillated acrylic fibers as the binder material, the product being air and water vapor permeable and providing the user protection from dangerous chemicals in liquid or gaseous form.

DESCRIPTION OF THE INVENTION INCLUDING PREFERRED EMBODIMENTS

In accordance with the present invention there is provided an air and water vapor permeable, toxic vapor absorptive, non-woven fabric material comprising
(a) fibrillated acrylic fibers, and
(b) an activated carbon constituent selected from the group consisting of activated carbon fiber, activated carbon paticles and mixtures of activated carbon fiber and activated carbon particles.

The novel products of the present invention are prepared by wet-laying the activated carbon constituent (activated carbon fibers and/or activated carbon particles) and fibrillated acrylic fibers from a water suspension thereof.

In the embodiment wherein the activated carbon constituent is a mixture of activated carbon fiber and activated carbon particles, the suspension should contain from about 5-25%, by weight, based on the total weight of fibers and particles, preferably from about 10-20%, by weight, of the fibrillated acrylic fibers, from about 10-75%, by weight, same basis, preferably from about 15-65%, by weight, of the activated carbon fiber and from about 15-80%, by weight, same basis, preferably from about 25-70%, by weight, of the activated carbon particles, the total weight of the three components being 100%.

In the embodiment of the invention wherein the activated carbon constituent is only activated carbon fiber, the concentration of fibrillated acrylic fiber may suitably range from about 5 to about 60% by weight, based on the total weight of the acrylic fibers and carbon fiber, and the concentration of the carbon fiber will be in the range of from about 40% to about 95%, by weight, on the same basis, the total weight of the two components being 100%.

In the embodiment of the invention wherein the activated carbon constituent is activated carbon particles, the concentration of fibrillated acrylic fiber suitably may be in the range of from about 35% to about 65%, by weight, based on the total weight of acrylic fibers and carbon particles, and the concentration of activated carbon particles suitably is in the range of from about 35% to about 65%, on the same basis, the total weight of the two components being 100%.

The activated carbon constituent (activated carbon particles and/or activated carbon fiber) and fibrillated acrylic fiber are wet-laid using the conventional papermaking process well known in the art. Flocculating agents and surface active agents can be incorporated into the water suspension in order to facilitate the paper making procedure as is also known in the art. The acrylic fiber may be produced from any known acrylic polymers such as polyacrylonitrile, copolymers of acrylonitrile and other copolymerizable monomers such as methyl methacrylate, ethyl acrylate etc; homopolymers and copolymers of other fiber forming monoethylenically unsaturated monomers such as vinyl acetate, vinyl chloride, styrene, vinyl pyridine, acrylic esters, acrylamide and the like.

Fibrillation of the acrylic fibers, which should range from about 1 mm to about 25 mm in length, is also accomplished as is known in the art i.e. such as by high speed shearing of the fibers.

The activated carbon fibers are also well-known in the art as are methods for their production. They can be used in lengths of from about 0.3 to about 15.0 mm, preferably from about 0.5 to about 10.0 mm, and can be prepared from such carbon fiber precursors as coal tar pitch, petroleum pitch, coal tar, petroleum derived thermal tar, ethylene tars, high-boiling coal tar distillates, ethylene tar distillates, gas oils or polynuclear aromatics. Also useful as precursors are polymers such as acrylonitrile homopolymers and copolymers, polyvinylalcohol, and natural and regenerated cellulose. Methods for preparing activated carbon fibers useful herein are disclosed in U.S. Pat. Nos. 4,069,297 and 4,285,831, which patents are heregy incorporated herein by reference.

The activated carbon powder or particles, have a particle size ranging from about 0.1 μm to about 100 μm, preferably from about 1.0 μm to about 80 μm and are also prepared from any of the carbon precursors described above.

Regardless of whether activated carbon fiber and/or activated carbon particles are utilized as the activated carbon constituent of the non-woven activated carbon fabric of this invention, the surface area of the carbon constituent, as measured by BET determination, desirably is greater than about 500 $M^2$/gm and preferably greater than about 1,000 $M^2$/gm. Although most commercially available activated carbon materials do not have surface areas greater than about 2600 $M^2$/gm, as measured by BET determination, the so-called very high surface area activated carbons which have surface area values as high as 3500 M²/gm are particularly advantageous in the practice of the present invention.

As associated with the desirability of providing a high degree of structural integrity to the non-woven fabric material of the present invention, it is preferred in practice that the particle size distribution of activated carbon particles utilized in the invention should include no more than 15% by weight of particles above 500 microns diameter and no more than 15% by weight of such particles below 10 microns diameter. Correspondingly, the particle size distribution of activated carbon fiber preferably includes no more than about 15% by weight of such particles of fiber diameter below about 1 micron and no more than about 15% by weight of such fibers with diameter above 100 microns. In general, it is satisfactory if the length of the carbon fibers is in the range of from about 100 microns up to about 2 centimeters.

The wet-lay sheet making process (papermaking) used herein for the production of the novel fabric material of the present invention, results in a product having unique sorptive characteristics, a thickness of at least about 0.005, preferably at least 0.01, inch, a high sorptive capacity to weight ratio and high porosity to fluid flow.

The preferred embodiment of the invention utilizes as the activated carbon constituent a mixture of activated carbon fiber and activated carbon particles. The equilibrum loading of absoptive carbon fiber in such embodiment is higher than conventional activated carbon powder products. The products of this embodiment the present invention are more porous than sheets containing only carbon particles. The carbon fiber, which tends to lay parallel to the plane of the sheet, produces a longer fluid flow path through the sheet which increases the time available to absorb impurities. The novel products of this embodiment accept an unexpectedly high additional loading of active carbon powder with only a small increase in fibrillated acrylic fiber as compared to conventional products, i.e. see U.S. Pat. No. 4,088,395. The combination of active carbon fiber and active carbon particles results in a higher performance versus cost ratio than sheets which contain only one of these active ingredients.

The surface of the novel fabric material of the present invention may be embossed during or after its production to improve sheet flexibility and/or porosity. The novel non-woven fabric material may be laminated to a woven, non-woven, knitted etc. backing such as matts, felts, papers, etc. produced from cotton, hemp, flax, ramie, jute, silk, wool, leather, flannel, flannelette, swansdown, poplin, cellulose ethers or esters, nylon, rayon, acetates, polythene, glass, rock wool, asbestos, in order to strengthen the material.

Lamination of the novel products hereof to the above-mentioned backing materials may be achieved by the use of water vapor and air permeable adhesives, preferably those available in the form of foams, such as rubber or acrylic latexes, polyurethanes and the like. These adhesives are self-adhering and upon curing foam and set into strong bonds.

The surface of the novel fabric material claimed herein may be rendered hydrophobic by coating with a porous silicone film or a polymer such as polytetrafluoroethylene. Additionally, a reactive coating capable of decomposing toxic agents, e.g. a coating of a sulfonated polymer to hydrolyze nerve gas, may be applied thereto so that the activated carbon particles and/or fibers form a second line of defense.

The fabric material of the present invention has a wide variety of uses. It is useful for protective purposes and for filtration and separation of gases. The uses include the manufacture of the fabric material into wearing apparel e.g., military uniforms; blankets, sleeping bags, bedding, surgical dressings, wrappers and containers, covers, tarpaulins, tents, curtains, gas masks, paint spraying masks, air-conditioning duct filters, flue gas deodorizers and the like.

The following examples are set forth for purposes of illustration only and are not to be construed as limitations on the present invention except as set forth in the appended claims. All parts and percentages are by weight unless otherwise specified.

EXAMPLE 1

A mixture of 14% fibrillated acrylic fibers, 18% activated carbon fiber and 68% activated carbon powder in 18 l. of water are formed into a sheet using a standard hand paper making machine. The sheet is dried under pressure at 70° C. to 120° C. The resultant fabric material is then tested. The results are set forth in Table I, below.

EXAMPLE 2

The procedure of Example 1 is again followed except that 12% fibrillated acrylic fiber, 59% activated carbon fiber and 29% active carbon powder are employed and the paper material is embossed after forming but before drying. The results are set forth in Table I, below.

EXAMPLE 3

The procedure of Example 2 is again followed except that the fabric material is not embossed. After drying the material is laminated to a 65/35 polycotton fabric utilizing a commercially available acrylic foam adhesive. The results are set forth in Table I, below.

EXAMPLE 4

The procedure of Example 1 is again followed except that 45% fibrillated acrylic fiber and 55% activated carbon powder are employed. No activated carbon fibers are present. The results are set forth below in Table I.

EXAMPLE 5

The procedure of Example 2 is again followed except that 6.3% fibrillated acrylic fiber and 93.7% activated carbon fiber are employed. No activated carbon particles are present. The results are set forth in Table I, below.

EXAMPLE 6

The procedure of Example 1 is again followed except that 19.4% fibrillated acrylic fiber, 80% activated carbon fiber and 0.6% polytetrafluoroethylene are employed. No activated carbon powder is present. The results are set forth in Table I, below.

EXAMPLE 7

The procedure of Example 2 is employed except that 6.3% of fibrillated acrylic fibers and 93.7% of activated carbon fibers are employed. No activated carbon powder is present. Two layers of the resultant fabric material are laminated as in Example 3. The results are set forth in Table I, below.

TABLE I

| Property | S | 1 | 2 | 3 | 4 | 5 | 6 | 7 |
|---|---|---|---|---|---|---|---|---|
| Weight (oz./yd$^2$) | 7.9 | 7.1 | 7.2 | 12.6 | 12.1 | 5.0 | 3.0 | 9.9 |
| Thickness (Inch) | 0.090 | 0.039 | 0.049 | 0.060 | 0.040 | 0.038 | 0.023 | 0.064 |
| Air Permeability (ft.$^3$/min/ft$^2$) | 46 | 5 | 21.4 | 15.5 | 0.6 | .39 | 21.1 | 93 |
| Water Vapor Transmission (gm/hr/M$^2$) | 74 | — | 85 | 54 | — | — | — | — |
| Tensile Test (lbs/in) | 36 | 18 | 18 | 65 | 44 | 2 | 6 | 2 |
| Flexibility (Taber-g/cm) | 3.1 | 16.0 | 7.0 | 16.0 | 36.5 | 9.8 | 14.0 | 22.0 |
| Static CCl$_4$ Absorption (mg/cm$^2$) | 14.9 | 7.5 | — | — | 15.1 | 5.6 | 2.2 | 10.5 |
| Static CCl$_4$ Sorptive Capacity (% fabric wt.) | 53.6 | 30.0 | — | — | 36.9 | 31.9 | 21.9 | 30.1 |
| Dynamic CCl$_4$ Absorption (mg/cm$^2$) | 2.5* | 2.0* | 3.5* | 4.3* | 6.7* | 0.85* | 0.05* | 1.35* |
| Dynamic CCl$_4$ Sorptive Cap. (% fabric wt.) | 9.0* | 8.0* | 14.4* | 10.1* | 16.3* | 4.8* | 0.5* | 3.9* |

*Calculated; based on 0.5 mg/l leakage point
S = Standard commercial product (nylon knit backed polyurethane foam cont. activated carbon powder)

We claim:

1. An air and water vapor permeable, toxic vapor absorptive, non-woven fabric material comprising a wet-laid sheet containing fibrillated acrylic fiber, activated carbon fiber and activated carbon particles, wherein the concentration of fibrillated acrylic fiber ranges from about 5–25% by weight based on the total weight of fibers and particles, the concentration of activated carbon fiber ranges from about 10–75% by weight, same basis, and the concentration of activated carbon particles ranges from about 15–80% by weight, same basis.

2. The fabric material of claim 1 wherein the fabric material surface is embossed.

3. The fabric material of claim 2 wherein a backing member is adhered thereto.

4. The fabric material of claim 1 wherein a backing member is adhered thereto.

* * * * *

REEXAMINATION CERTIFICATE (1002nd)
United States Patent [19]
Giglia et al.

[11] B1 4,565,727
[45] Certificate Issued Jan. 24, 1989

[54] NON-WOVEN ACTIVATED CARBON FABRIC

[75] Inventors: Robert D. Giglia, Rye, N.Y.; Edward A. Battistelli, Stratford, Conn.

[73] Assignee: American Cyanamid Co., Stamford, Conn.

Reexamination Request:
No. 90/001,420, Jan. 11, 1988

Reexamination Certificate for:
Patent No.: 4,565,727
Issued: Jan. 21, 1986
Appl. No.: 725,527
Filed: Apr. 23, 1985

[51] Int. Cl.$^4$ .......................... B32B 5/16; B32B 7/14; B32B 31/00
[52] U.S. Cl. .................... 428/172; 428/281; 428/283; 428/286; 428/299; 428/297; 428/408; 428/367; 162/146; 210/505; 210/508; 210/509; 210/510; 55/527; 55/528
[58] Field of Search ............... 428/171, 172, 281, 283, 428/286, 367, 408, 288, 297, 298, 299; 162/146; 210/505, 508, 509, 510; 55/527, 528

[56] References Cited

U.S. PATENT DOCUMENTS

3,826,712   7/1974   Masuda et al. ............... 162/157 R

FOREIGN PATENT DOCUMENTS

2216377   8/1974   France .

*Primary Examiner*—Nancy A. B. Swisher
*Attorney, Agent, or Firm*—Frank M. Van Reit

[57] ABSTRACT

An air and water vapor permeable, toxic vapor absorptive non-woven fabric material comprising a web-laid sheet containing fibrillated acrylic fiber, and an activated carbon constituent selected from the group consisting of activated carbon fiber, activated carbon particles, and mixtures of activated carbon fiber and activated carbon particles.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–4 dependent on an amended claim, are determined to be patentable.

1. An air and water vapor permeable, toxic vapor absorptive, non-woven fabric material comprising a wet-laid sheet containing fibrillated acrylic fiber, activated carbon fiber and activated carbon particles *having a particle size ranging from about 0.1 μm to about 100 μm*, wherein the concentration of fibrillated acrylic fiber ranges from about 5–25% by weight based on the total weight of fibers and particles, the concentration of activated carbon fiber ranges from about 10–75% by weight, same basis, and the concentration of activated carbon particles ranges from about 15–80% by weight, same basis.

* * * * *